(12) United States Patent
Ling et al.

(10) Patent No.: US 8,873,710 B2
(45) Date of Patent: Oct. 28, 2014

(54) MULTI-SOURCE RADIATION SYSTEM AND METHOD FOR INTERWOVEN RADIOTHERAPY AND IMAGING

(75) Inventors: C. Clifton Ling, New York, NY (US); Margie A. Hunt, Larchmont, NY (US); Pengpeng Zhang, Great Neck, NY (US); Athanasios Etmektzoglou, Milpitas, CA (US); Edward Shapiro, Menlo Park, CA (US)

(73) Assignees: Sloan-Kettering Institute for Cancer Research, New York, NY (US); Varian Medical Systems, Inc., Palo Alto, CA (US)

( * ) Notice: Subject to any disclaimer, the term of this patent is extended or adjusted under 35 U.S.C. 154(b) by 324 days.

(21) Appl. No.: 13/398,206

(22) Filed: Feb. 16, 2012

(65) Prior Publication Data
US 2012/0230464 A1    Sep. 13, 2012

Related U.S. Application Data

(60) Provisional application No. 61/449,867, filed on Mar. 7, 2011, provisional application No. 61/511,327, filed on Jul. 25, 2011.

(51) Int. Cl.
*A61N 5/10*    (2006.01)
*A61B 6/03*    (2006.01)
*A61B 6/00*    (2006.01)

(52) U.S. Cl.
CPC ....... *A61N 5/1047* (2013.01); *A61N 2005/1061* (2013.01); *A61B 6/032* (2013.01); *A61N 5/1065* (2013.01); *A61B 6/4085* (2013.01)
USPC ............................................................ 378/65

(58) Field of Classification Search
USPC ............................................................ 378/65
See application file for complete search history.

(56) References Cited

U.S. PATENT DOCUMENTS 5,548,627 A * 8/1996 Swerdloff et al. .............. 378/65
7,221,733 B1   5/2007 Takai et al.
(Continued)

FOREIGN PATENT DOCUMENTS

EP    1419800 A1    5/2004
EP    0814869 B1    12/2004

OTHER PUBLICATIONS

Notification of Transmittal of the International Search Report and the Written Opinion of the International Searching Authority, or the Declaration for PCT Application No. PCT/US2012/025382, dated Aug. 19, 2013 (11 pages).
(Continued)

*Primary Examiner* — Glen Kao
(74) *Attorney, Agent, or Firm* — Kevin P. Radigan, Esq.; Heslin Rothenberg Farley & Mesiti P.C.

(57) ABSTRACT

An arc radiotherapy and imaging system is provided which includes a first radiation source and a second radiation source. The first radiation source is suitable for treating a region of a patient, and the second radiation source is suitable for imaging the region of the patient. A control is also provided for automatically adjusting system operation, according to a defined schedule, between treating the region of the patient using the first radiation source and imaging the region of the patient using the second radiation source, thereby facilitating both treating and imaging of the region of the patient.

18 Claims, 9 Drawing Sheets

(56) References Cited

U.S. PATENT DOCUMENTS

| | | | |
|---|---|---|---|
| 7,657,304 | B2 | 2/2010 | Mansfield et al. |
| 7,945,021 | B2 | 5/2011 | Shapiro et al. |
| 2004/0264640 | A1 | 12/2004 | Myles |
| 2005/0273659 | A1 | 12/2005 | Shaw |
| 2006/0050847 | A1* | 3/2006 | Jaffray et al. ............ 378/65 |
| 2008/0226018 | A1 | 9/2008 | Partain et al. |
| 2008/0273659 | A1 | 11/2008 | Guertin et al. |
| 2009/0067579 | A1 | 3/2009 | Mansfield |
| 2009/0190714 | A1 | 7/2009 | Partain |
| 2009/0208074 | A1 | 8/2009 | Wiersman et al. |
| 2009/0252291 | A1* | 10/2009 | Lu et al. .................. 378/65 |
| 2010/0195792 | A1 | 8/2010 | Kunz et al. |
| 2010/0202587 | A1* | 8/2010 | Schmidt et al. ........... 378/65 |
| 2010/0246753 | A1 | 9/2010 | Mollov |
| 2010/0310042 | A1 | 12/2010 | Fox et al. |
| 2010/0316259 | A1 | 12/2010 | Liu et al. |
| 2011/0080990 | A1 | 4/2011 | Filiberti et al. |
| 2012/0002786 | A1* | 1/2012 | Bani-Hashemi et al. .... 378/65 |
| 2012/0039433 | A1 | 2/2012 | Berkus et al. |

OTHER PUBLICATIONS

Adamson et al. "Dosimetric effect of intrafraction motion and residual setup error for hypofractionated prostate intensity-modulated radiotherapy with online cone beam computed tomography image guidance". International Journal of Radiat. Oncol. Biol. Phys., vol. 80, pp. 453-461 (2011).

Dawson et al. "Advances in image-guided radiation therapy", Journal of Clinical Oncology, vol. 25, pp. 938-946 (2007).

Godfrey et al. "Digital tomosynthesis with an on-board kilovoltage imaging device", International Journal of Radiat. Oncol. Biol. Phys., vol. 65, pp. 8-15 (2006).

Kupelian et al. "Daily variations in delivered doses in patients treated with radiotherapy for localized prostate cancer", International Journal of Radiat. Oncol. Biol. Phys., vol. 66, pp. 876-882 (2006).

Langen et al. "Observations on real-time prostate gland motion using electromagnetic tracking", International Journal of Radiat. Oncol. Biol. Phys., vol. 71, pp. 1084-1090 (2008).

Li et al. "Dosimetric consequences of intrafraction prostate motion", International Journal of Radiat. Oncol. Biol. Phys., vol. 71, pp. 801-812 (2008).

Ling et al. "Dose-rate effects in external beam radiotherapy redux", Radiother. Oncol., vol. 95, pp. 261-268 (2010).

Ling et al. "From IMRT to IGRT: Frontierland or Neverland?", Radiother. Oncol., vol. 78, pp. 119-122 (2006).

Ling et al. "Commissioning and quality assurance of RapidArc radiotherapy delivery system", International Journal of Radiat. Oncol. Biol. Phys., vol. 72, pp. 575-581 (2008).

LoSasso et al. "Comprehensive quality assurance for the delivery of intensity modulated radiotherapy with a multileaf collimator used in the dynamic mode", Med. Phys., vol. 28, pp. 2209-2219 (2001).

McBain et al. "X-ray volumetric imaging in image-guided radiotherapy: the new standard in non-treatment imaging", International Journal of Radiat. Oncol. Biol. Phys., vol. 64, pp. 625-634 (2006).

Nakagawa et al. "First clinical cone-beam CT imaging during volumetric modulated arc therapy", Radiother. Oncol., vol. 90, pp. 422-423 (2009).

Nakagawa et al. "Verification of in treatment tumor position using kilovoltage cone-beam computed tomography: a preliminary study", International Journal of Radiat. Oncol. Biol. Phys., vol. 69, pp. 970-973 (2007).

Otto, K. "Volumetric modulated arc therapy: IMRT in a single gantry arc", Med. Phys., vol. 35, pp. 310-317 (2008).

Park et al. "Four-dimensional cone-beam computed tomography and digital tomosynthesis reconstructions using respiratory signals extracted from transcutaneously inserted metal markers for liver SBRT", Med. Phys., vol. 38, pp. 1028-1036 (2011).

Song et al. "Respiratory motional effect on cone-beam CT in lung radiation surgery", Med. Dosim., vol. 34, pp. 117-125 (2009).

Star-Lack et al. "Optimization of FDK reconstruction parameters to minimize aliasing and reduce metal artifacts", Med. Phys., vol. 34, pp. 2341-2342 (2007).

Sun et al. "Improved scatter correction using adaptive scatter kernel superposition", Phys. Med. Biol., vol. 55, pp. 6695-6720 (2010).

Tanyi et al. "Volumetric image guidance: does routine usage prompt adaptive re-planning? An institutional review", Acta. Oncol., vol. 47, pp. 1444-1453 (2008).

Timmerman, R.D. "An overview of hypofractionation and introduction to this issue of seminars in radiation oncology", Semin. Radiat. Oncol., vol. 18, pp. 215-222 (2008).

Williams et al. "The effects of radiation scatter from simultaneous MV irradiation on kV fluoroscopic and X-ray volume imaging with Elekta Synergy System", (Abstract), Radiother. Oncol., vol. 73, pp. S229-230 (2004).

Xing et al. "Overview of image-guided radiation therapy", Med. Dosim., vol. 31, pp. 91-112 (2006).

Yan et al. "Adaptive modification of treatment planning to minimize the deleterious effects of treatment setup errors", International Journal of Radiat. Oncol. Biol. Phys., vol. 38, pp. 197-206 (1997).

Zhang et al. "Volumetric modulated arc therapy: planning and evaluation for prostate cancer cases", International Journal of Radiat. Oncol. Biol. Phys., vol. 76, pp. 1456-1462 (2010).

Zhang et al. "Optimization of collimator trajectory in volumetric modulated arc therapy: development and evaluation for paraspinal SBRT", International Journal of Radiat. Oncol. Biol. Phys., vol. 77, pp. 591-599 (2010).

Ling et al. "Acquisition of MV-Scatter-Free Kilovoltage CBCT Images During RapidArc or VMAT", Radiother. Oncol., vol. 100, pp. 145-149 (2011).

Kida et al. "CBCT Reconstruction during VMAT Delivery Using Elekta Synergy System", Med. Phys., vol. 37, p. 3107 (2010).

Poludniowski et al. "CT reconstruction from portal images acquired during volumetric-modulated arc therapy", Phys. Med. Biol., vol. 55, pp. 5635-5651 (2010).

Nakagawa et al. "Cone beam computed tomography data acquisition during VMAT delivery with subsequent respiratory phase sorting based on projection image cross-correlation", J. Radiat. Res., vol. 52, pp. 112-113 (2011).

* cited by examiner

VMAT - CBCT METHOD: COMPRESSED DELIVERY + SIMULTANEOUS IMAGING

PLAN (GIVEN) PARAMETERS:
TOTAL MU
MAXIMUM DOSE RATE: $DR_{max}$
CONTROL POINTS: $N_{cp}$ (500)
  DELIVERY: $0.5*N_{cp}$
  IMAGING: $0.5*N_{cp}$
PROJECTIONS REQUIRED ($N_I$ = 660)
SAMPLE RATE f = 11/SEC CALCULATED PARAMETERS:
1. TIME FOR ONE ROTATION: $T = \max[N_I/f + MU/DR_{max}), (\frac{V_{gmax}}{360})]$
2. MINIMUM NUMBER OF IMAGES TAKEN FOR AN IMAGING cp IS 1, THEREFORE MINIMUM GANTRY INTERVAL FOR AN IMAGING cp:
   $\Delta g_I^j = 360/(N_{cp}/2) - 0.5\Delta g_D^j - 0.5\Delta g_D^{j+1} > 360/(Tf)$
3. GANTRY INTERVAL FOR A DELIVERY cp,
   $\Delta g_D^j = 360*(MU^j/DR_{max})/T$
4. MAXIMUM POSSIBLE MU PER cp:
   $MU_{max}^j = DR_{max}(2T/N_{cp} - 1/f)$
5. MAXIMUM POSSIBLE MU FOR A PLAN:
   $0.5N_{cp}MU_{max}^j = DR_{max}(T - 0.5N_{cp}/f)$

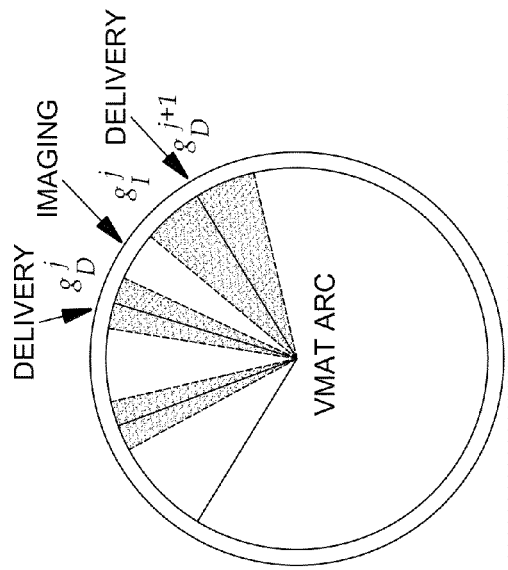

SPLIT EACH DOSE DELIVERY CP, DELIVER DOSE WITH MAXIMUM DOSE RATE, USE TIME SAVED BETWEEN THE TWO DELIVERY CONTROL POINTS FOR SCATTER FREE CBCT PROJECTIONS

FIG. 3A

MULTI-SOURCE RADIATION SYSTEM AND METHOD FOR INTERWOVEN RADIOTHERAPY AND IMAGING

CROSS-REFERENCE TO RELATED APPLICATIONS

This application claims the benefit of U.S. provisional application Ser. No. 61/449,867, filed Mar. 7, 2011, entitled "Multi-Source Radiation System and Method for Interleaved Radiotherapy and Imaging", and also claims the benefit of U.S. provisional application Ser. No. 61/511,327, filed Jul. 25, 2011, entitled "Acquisition of MV Scatter-Free Kilovoltage CBCT Images During RapidArc™", the entirety of each of which is incorporated herein by reference.

BACKGROUND

This invention relates generally to radiation systems, and more particularly, to radiation systems having treatment and imaging capabilities.

Radiation therapy involves medical procedures that selectively expose a region of a patient, such as a cancerous tumor, to doses of radiation. The purpose of the radiation therapy is to irradiate the targeted region (e.g., the targeted biological tissue) till the undesirable tissue is destroyed. Radiation has also been used to obtain images of tissues for facilitating planning or subsequent treatment.

During a radiation planning session, radiation treatment planning is performed before treatment radiation is delivered to a patient. This allows an accurate and precise dosage of radiation to be delivered to the patient. During the planning session, configuration data, such as location, size, and shape of a targeted region, may be acquired from an imaging procedure, performed (for example) using a computed tomography (CT) imaging system. Existing CT imaging systems typically take image slices of a patient in which the image slices are vertical (or perpendicular) to a longitudinal axis of the patient or the patient support.

After the radiation treatment plan is determined, the patient then undergoes a radiation treatment procedure. During the radiation treatment procedure, a radiation treatment system is used to deliver a desired radiation dosage to the targeted region of the patient according to the determined radiation treatment plan. In existing radiation treatment systems, the radiation source that generates the radiation beam is configured to rotate within a plane that is substantially vertical (or perpendicular) to a longitudinal axis of the patient or the patient support. Varying the intensity and the entry angle of the incident radiation beam allows a radiation specialist to generate a radiation dose volume that corresponds to the size, shape, and location of the targeted object.

BRIEF SUMMARY

In accordance with an aspect of the present invention, an arc radiotherapy and imaging system is provided which includes a first radiation source and a second radiation source. The first radiation source is suitable for treating a region of a patient, and the second radiation source is suitable for imaging the region of the patient. The arc radiotherapy and imaging system further includes a control for automatically adjusting system operation, according to a defined schedule, between treating the region of the patient using the first radiation source, and imaging the region of the patient using the second radiation source, thereby facilitating both treating and imaging of the region of the patient.

In another aspect of the present invention, a method is disclosed, which includes: providing a first radiation source suitable for treating a region of a patient; providing a second radiation source suitable for imaging the region of the patient; and providing a control for automatically adjusting system operation, according to a defined schedule, between treating the region of the patient using the first radiation source and imaging the region of the patient using the second radiation source, thereby facilitating both treating and imaging of the region of the patient.

Additional features and advantages are realized through the techniques of the present invention. Other embodiments and aspects of the invention are described in detail herein and are considered a part of the claimed invention.

BRIEF DESCRIPTION OF THE SEVERAL VIEWS OF THE DRAWINGS

One or more aspects of the present invention are particularly pointed out and distinctly claimed as examples in the claims at the conclusion of the specification. The foregoing and other objects, features, and advantages of the invention are apparent from the following detailed description taken in conjunction with the accompanying drawings in which:

FIG. 3A is a further schematic illustration of a geometrical aspect of a technique for interwoven radiotherapy and imaging, in accordance with one or more aspects of the present invention;

DETAILED DESCRIPTION

Various embodiments are described below with reference to the figures, which are not drawn to scale. It should also be noted that the figures are examples only, that are intended to facilitate the description of certain embodiments. They are not intended as an exhaustive description of the invention or as a limitation on the scope of the invention. In addition, an aspect described in conjunction with a particular embodiment is not necessarily limited to that embodiment, and can be practiced in other embodiments. Moreover, alternative configurations, components, methods, etc., discussed in conjunction with one or more of the embodiments can be used in connection with other embodiments, even if such other embodiments do not discuss such alternatives or discuss different alternatives.

Figure 1:
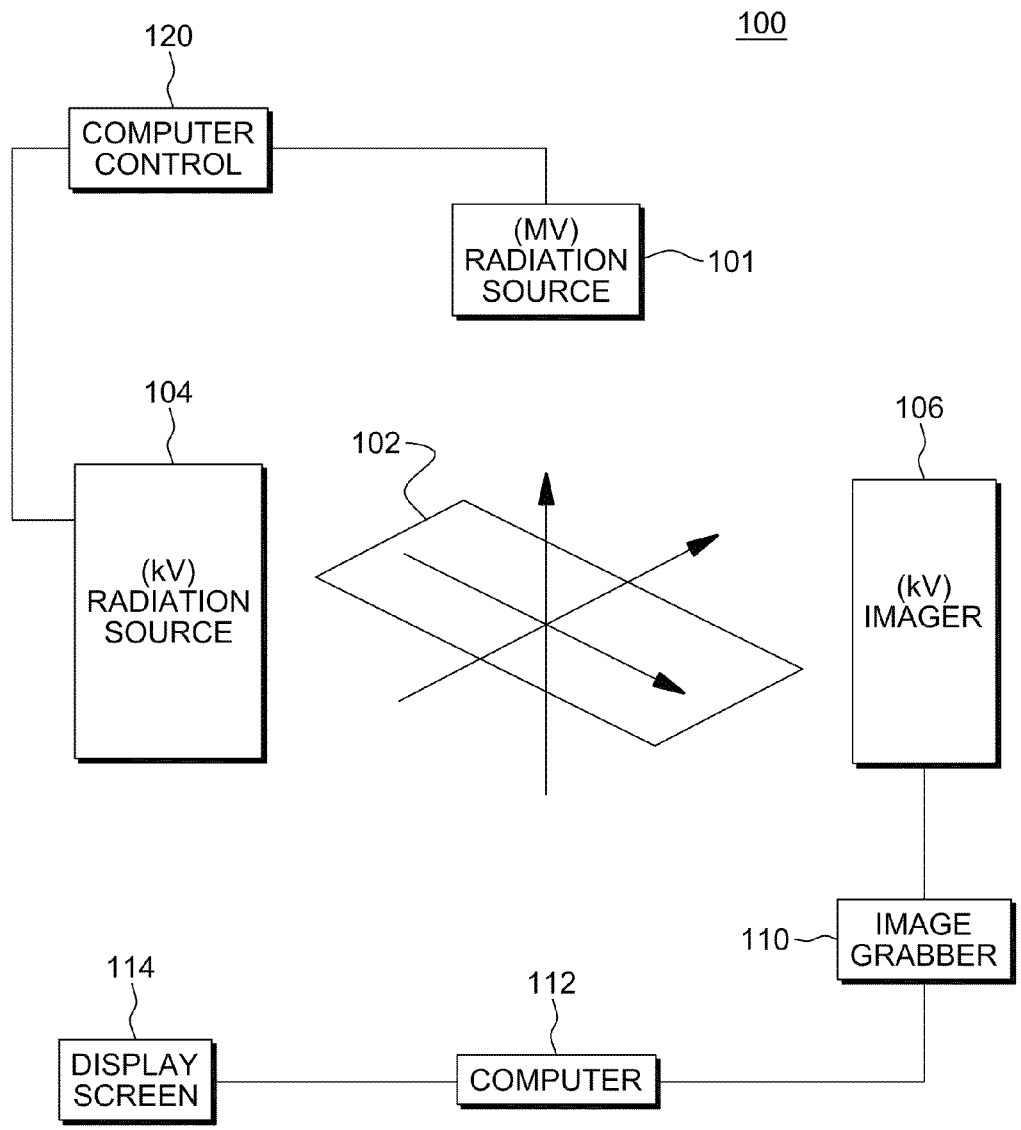
FIG. 1 is a schematic diagram of one embodiment of an arc radiotherapy and imaging system, in accordance with one or more aspects of the present invention.

FIG. 1 is a schematic representation of one embodiment of an arc radiotherapy and imaging system 100 for interwoven (or interleaved) radiotherapy and imaging, in accordance with one or more aspects of the present invention. As described below, a first radiation source, suitable for treating a region of a patient, and a second radiation source, suitable for imaging the region of a patient, are provided as part of the arc radiotherapy and imaging system. (Note that, as used herein, the "region" of the patient may comprise a portion of the patient, and in one example, may be a targeted biological tissue or object within or on the patient.) In addition, a controller (or control) is provided for automatically adjusting system operation, according to a defined schedule, between treating the patient using the first radiation source and imaging the patient using the second radiation source, to facilitate (in one embodiment) automated, interwoven treating and imaging of the patient.

In the example of FIG. 1, a megavoltage (MV) radiation source 101 emits a treatment radiation beam to a patient (not shown), or more particularly, a region of a patient, supported on a couch 102. Couch 102, upon which the patient rests, is positioned in the path of the MV beam. MV radiation source 101, in one embodiment, is coupled to an accelerator gantry (not shown) to rotate relative to couch 102 during the arc radiotherapy treatment. In one implementation, a linear accelerator, such as the TrueBeam® linear accelerator, offered by Varian Medical Systems, Inc., Palo Alto, Calif., may be employed within the system (which would comprise the MV radiation source 101).

As explained further below, interwoven with the arc radiotherapy treatments, image data is accumulated via (in one embodiment) a kilovoltage (kV) imaging system comprising a kV radiation source 104 and a kV imager 106. Although not shown, kV radiation source 104 and kV imager 106 may also be coupled to the accelerator gantry to rotate relative to couch 102 during the accumulation of kV projections. As illustrated, kV imager 106 is connected to an image grabber 110, which acquires kV image data during the imaging portion of the interleaved radiotherapy and imaging method disclosed herein. Computer 112 combines the acquired kV image data with, for example, patient position information, and/or other data, which can then (for example) be displayed in real time on a display screen 114.

Note that although described herein as advantageously employing a kV radiation source 104 and kV imager 106, the interweaving of treating and imaging of the patient may employ other imaging approaches, such as megavoltage (MV) cone-beam computed tomography (CBCT) projections. Further, note that the defined schedule for switching operation may accommodate, by way of example, any one of regularly spaced imaging control points or irregularly spaced imaging control points interspersed with treatment control points that facilitate treating the region of the patient using the MV radiation source 101. Note also that an MV imaging system with MV imaging control points could be combined with a kV imaging system with kV imaging control points, or may be used in place of the kV imaging system in imaging the region of the patient.

In accordance with the present invention, a computer control 120, which may comprise the same computer(s) as computer 112, or a different computer(s), is coupled to MV radiation source 101 and kV radiation source 104 for controlled, automated adjusting or synchronization of system operation, for example, according to a defined schedule, between treating a region of a patient using the MV radiation source and imaging the region of the patient using the kV radiation source.

More particularly, disclosed herein (in one embodiment) is the concept of acquiring kV images, such as kV cone-beam computed tomography (CBCT) images, during (or interwoven with) treatment delivery using, for example, volume modulated arc therapy (VMAT) or intensity modulated radiation therapy (IMRT). VMAT and IMRT are forms of external beam radiotherapy during which treatment is given using a megavoltage (MV) x-ray beam as the accelerator gantry moves around the patient. As the gantry rotates, various machine parameters are modified at different treatment control points or segments to deliver a conformal dose distribution to the targeted region. Note that as used herein, and unless otherwise indicated, "control point" and "segment" are used interchangeably. By way of example, a control point is a point or segment for which machine parameters are set, that is, up to a next control point or segment. Note also that with the imaging approaches disclosed herein, images are concomitantly obtained during the time session that treatment is given.

In one detailed embodiment, to obtain CT images during (for example) VMAT delivery, the method of VMAT delivery is modified. VMAT delivery is normally planned with a series of control points (which define a series of many (e.g., 200) small arc segments of mini-beams), each with its own set of machine parameters. In accordance with an aspect of the present invention, the number of control points, and thus the number of segments, is increased. In one example, this increase may be by a factor of two. However, the number of control points (or segments) may be increased as needed to, for example, facilitate imaging every two treatment segments, every three treatment segments, etc., according to any desired regular or irregular schedule. Any of these sequence combinations is considered to comprise interwoven treating and imaging of the patient, as used herein.

Figure 2A:
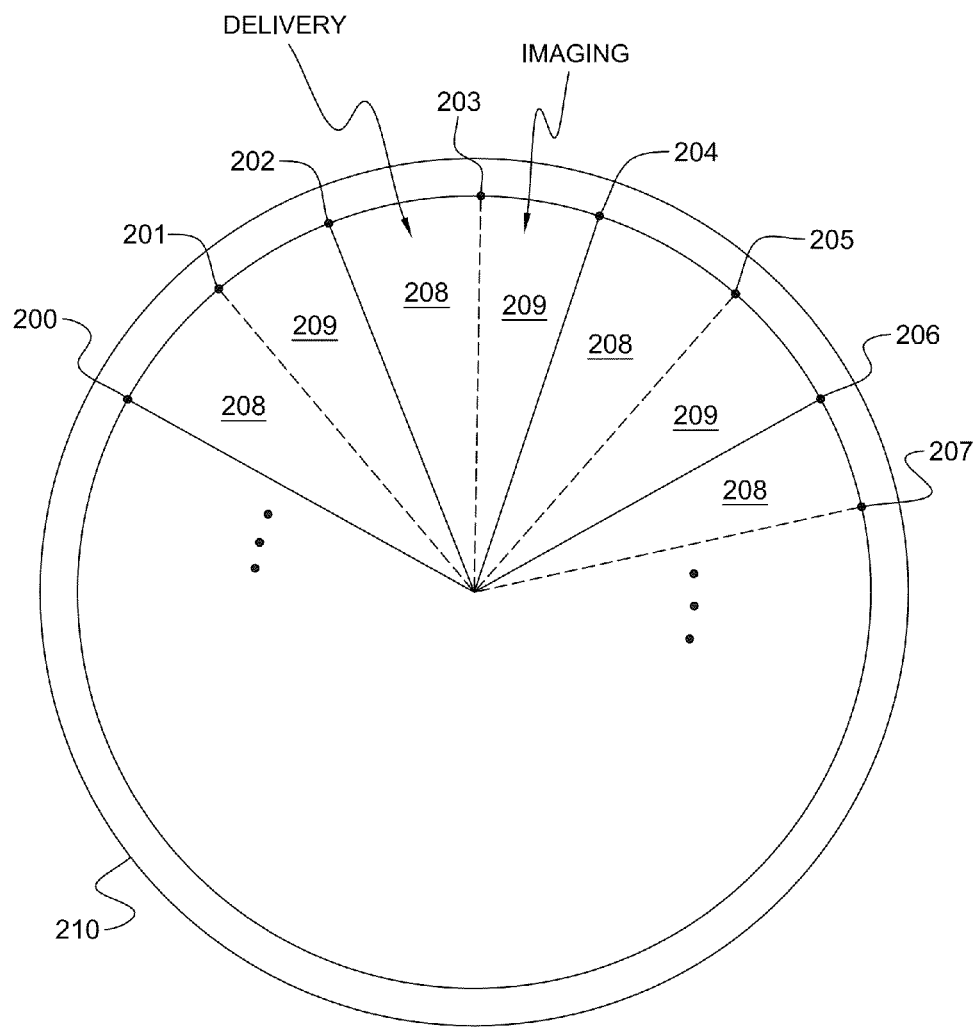
FIG. 2A is a schematic illustration of a geometrical aspect of a technique for interwoven radiotherapy and imaging, in accordance with one or more aspects of the present invention.

In the specific example illustrated in FIG. 2A, the number of control points (and arc segments) is assumed to be increased by a factor of two, with each original treatment segment being divided into two parts, one for treatment delivery, and the other for imaging. More particularly, VMAT delivery may be planned as a series of treatment control points 200, 202, 204, 206, etc., defining small arc segments between the points, each with its own set of machine parameters. In accordance with the present invention, the arc segments between adjacent treatment control points are divided, for example, in half, and imaging control points 201, 203, 205, 207, etc. are added, thereby forming (in this example) alternating treatment segments 208 and imaging segments 209. In one implementation, during the imaging segments 209, no (or minimal) MV radiation treatment dose is provided to minimize the amount of MV radiation being delivered, thereby minimizing the amount of MV scatter radiation to the kilovoltage imager. This improves image quality, as discussed further below.

Figure 2B:
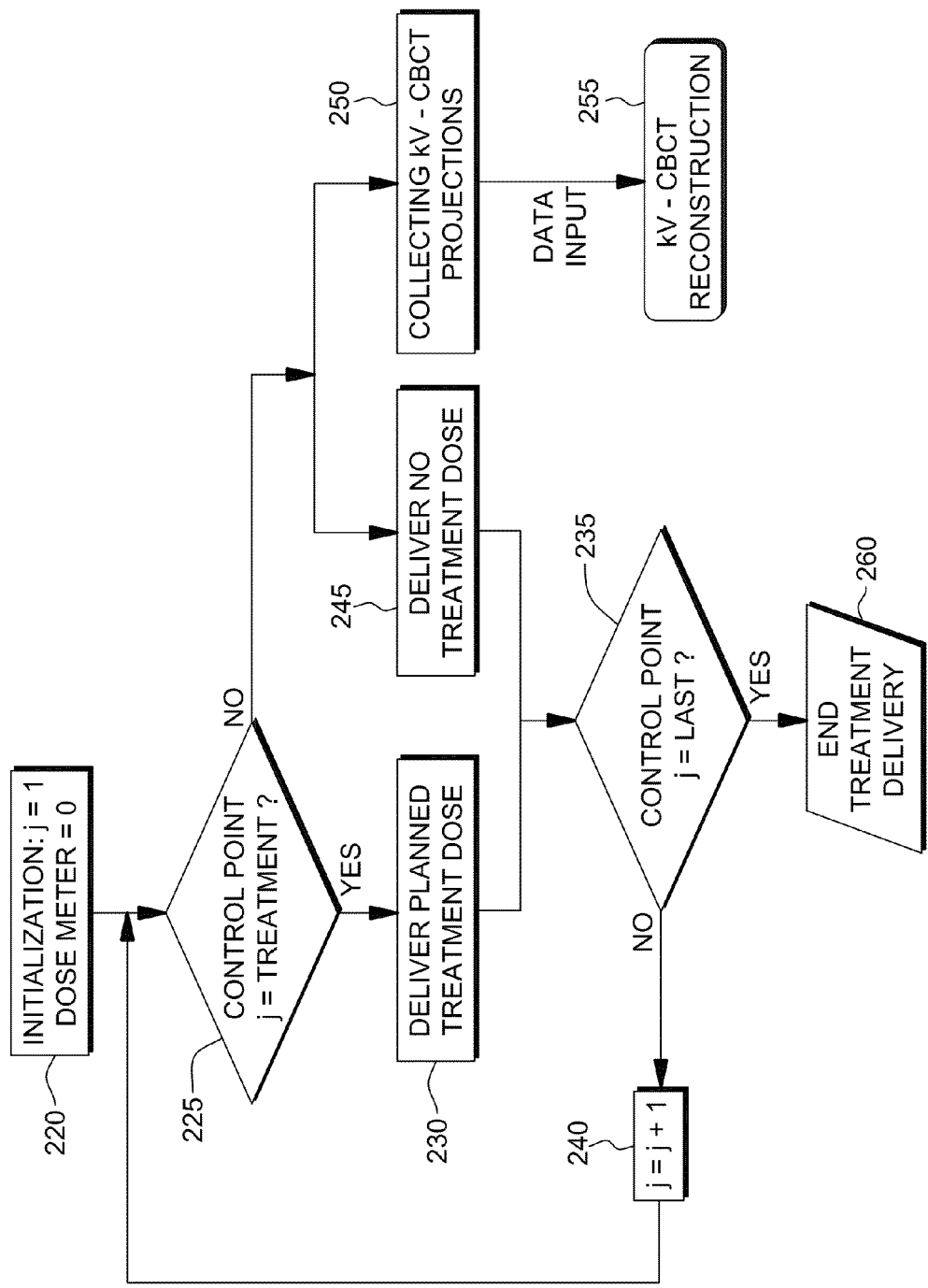
FIG. 2B is a flowchart of one embodiment of a process for interwoven radiotherapy and imaging, in accordance with one or more aspects of the present invention.

FIG. 2B illustrates one embodiment of a process for interleaved arc radiotherapy and imaging, in accordance with one or more aspects of the present invention. In this process embodiment, arc therapy delivery is interwoven with CBCT acquisition, as described above.

The system is initialized, for example, by setting a control point variable "j" equal to 1, the dose meter to zero, etc., 220. Processing determines whether a next control point j is a treatment control point 225, and if "yes", then the planned treatment dose is delivered via, for example, the MV radiation source 230. Processing then determines whether control point j is the last control point in the sequence of control points to be processed during the treatment session 235, and if "no", control point j is incremented by 1, and processing returns to determine whether the then current control point j is another treatment control point 225. As noted above, treatment control points and imaging control points may alternate, or multiple treatment control points may be processed before processing an imaging control point (or vice versa). The schedule of processing and imaging control points is predefined as a regular or irregular pattern, as desired for a particular implementation.

If the current control point is an imaging control point, then processing delivers no (or minimal) treatment dose 245 and concurrently collects, for example, at least one kV-CBCT projection 250. This data is input to the imaging computer for kV-CBCT reconstruction 255 using conventional processes. Once the last control point j in the planned sequence of control points has been processed, the treatment delivery session is ended 260.

As a further enhancement, the treatment segments for, for example, VMAT delivery, may be optimally compressed, and the imaging segments expanded. This can allow a maximum number of images to be acquired during the scheduled VMAT delivery session, thereby providing optimal image quality in the shortest time. FIG. 3A illustrates one embodiment for accomplishing compression of treatment delivery and simultaneous imaging. In this example, it is assumed that gantry speed is constant for the entire treatment plan. However, the concepts disclosed herein could also be employed with a variable gantry speed arc radiotherapy system. In a system with non-uniform gantry speed, attributes such as dose being delivered, dose rate, multi-leaf collimator (MLC) motion, collimator rotation, etc., may need to be considered to ascertain, for example, a maximum number of CT images which may be acquired during a scheduled VMAT delivery session.

In FIG. 3A, the following terms are employed:
$g_D^j$: center of the gantry interval (or segment) at the $j^{th}$ control point, delivering full dose
$g_I^j$: center of the gantry interval (or segment) at the $j^{th}$ control point, delivering no/minimal dose, designed to collect MV-scatter free projections
$DR_{max}$: maximum dose rate used for dose delivery
$N_{cp}$: number of control points used in an XML file that commands the linear accelerator for delivery:
Among Ncp, both delivery and imaging occupy half (0.5*Ncp). Maximum for today's linear accelerator is 500. (Note: Treatment and imaging each occupying one-half (0.5) of the control point is provided by way of example only.)
$N_f$: number of projections, minimal 660 and 340 for half-fan and full-fan mode, respectively
f: frames per second
MU: monitor units
$V_{gmax}$: maximum gantry speed (e.g., 1 RPM).
Also, the kV projections may be (in one example) collected at a frame rate per second, $f_r=11$/sec.

Figure 3B:
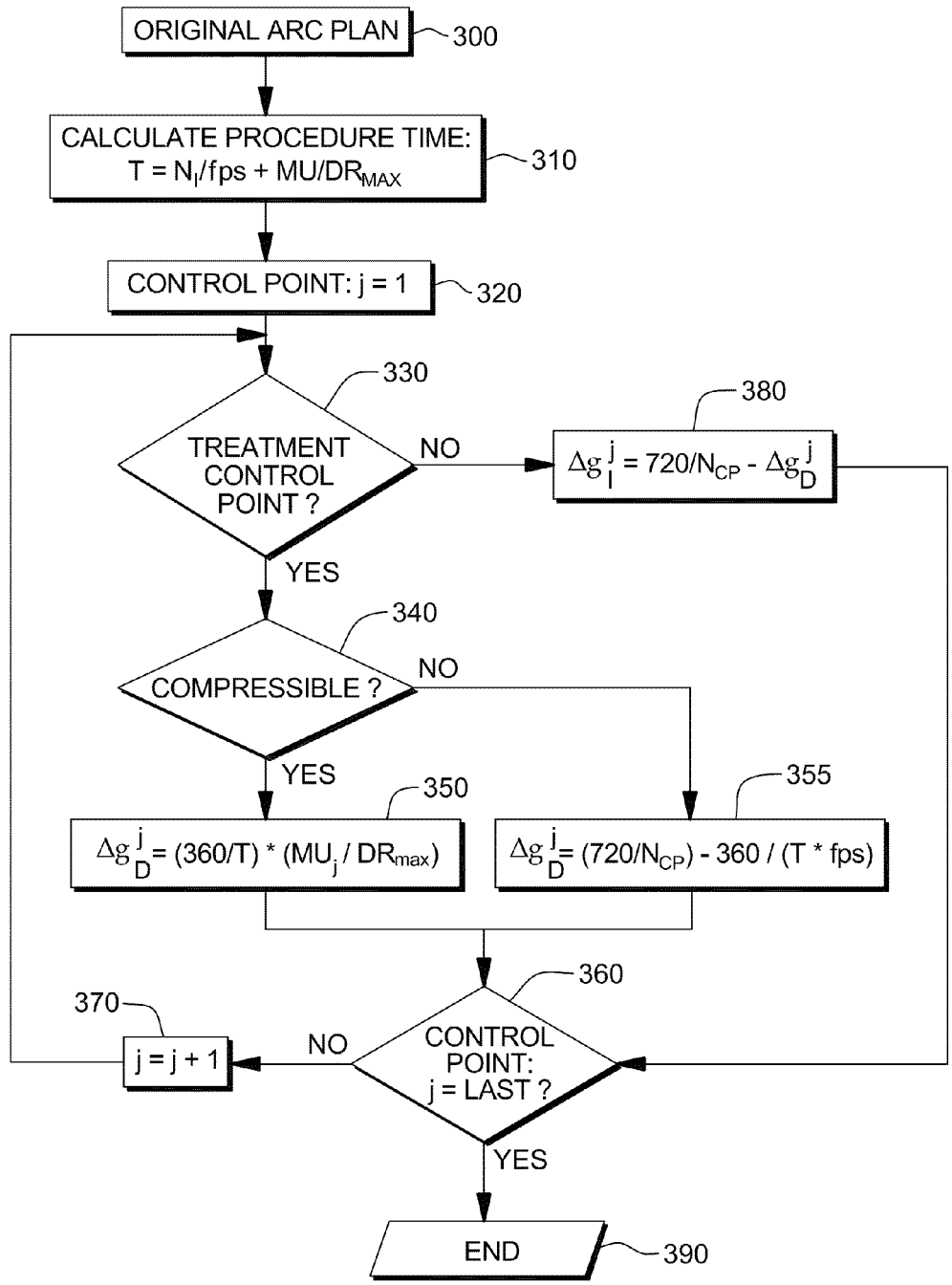
FIG. 3B is a flowchart of one embodiment of a process for determining gantry intervals for interwoven radiotherapy and imaging, in accordance with one or more aspects of the present invention.

FIG. 3B depicts one embodiment of the processing approach illustrated in FIG. 3A, wherein, by way of example, 360 imaging CPs (or segments) are being introduced into a control plan. An original arc plan for treatment delivery is obtained 300, and processing calculates a procedure time T 310. The control point variable j is set to 1 320, and processing determines whether the control point is a treatment control point 330. If "yes", then processing determines whether the treatment control point is compressible 340. If the treatment is compressible, the gantry $\Delta g_D^j$ for control point j is determined using a first algorithm 350, and if not compressible, is determined using a second algorithm 355. In the first algorithm 350, the control point j is compressible if the dose required in that control point can be delivered in a smaller gantry interval by increasing the machine dose rate. If this can be done, then the adjacent gantry interval for imaging can be expanded to allow the acquisition of additional projections. If no control point compression is possible, then the gantry interval for treatment is set to the maximum allowed, and the minimum number of projections are acquired. Once the gantry interval (i.e., arc segment) is determined, processing determines whether control point j is the last control point 360, and if "no", increments the variable j by 1, and returns to determine whether the next control point is a treatment control point 330. If the next control point is an imaging control point, processing determines the gantry interval for the imaging segment $\Delta g_I^j$ 380, before returning to determine whether control point j is a last control point in the plan 360. The minimum gantry interval for an imaging control point is the difference between the total gantry interval between two adjacent treatment control points and the gantry interval of the first treatment control point. Once the last control point has been processed, processing ends 390.

To restate, and by way of more specific example, disclosed herein is a clinical application of true integration of dose delivery and imaging through programmed sequencing, implemented (in one embodiment) on the platform of a TrueBeam® linear accelerator. The direct output, kilovoltage (kV) cone-beam computed tomography (CBCT) acquired during volumetric-modulated arc therapy (VMAT) using, for example, RapidArc® (offered by Varian Medical Systems, Palo Alto, Calif.) delivery with minimal MV scatter, can serve as essential information for patient treatment recording and verification. This novel methodology, as well as the resulting volumetric image set, can facilitate image-guided radiation therapy, and adaptive radiation therapy.

KV CBCT acquired during RapidArc® can provide essential information describing how treatment was actually delivered. While intra-treatment motion trajectory can be resolved by other means, true dose delivered to target, as well as surrounding normal tissues can be determined through CBCT, serving as either a treatment record for future outcome studies, or a departure point for later treatment adaptation.

Since CBCT images acquired concomitantly with radiation treatment delivery may be negatively affected by the scatter from the MV beam, a method is provided herein to obtain CBCT images with minimal MV scatter. Proof-of-principle studies were performed to demonstrate such capabilities on the platform of TrueBeam®.

A standard RapidArc® plan comprises hundreds of control points (CPs) that direct the linear accelerator (linac) to deliver planned dose(s) with designed multi-leaf collimator (MLC) aperture and dose rate within a certain gantry range. In accordance with an aspect of the present invention, the treatment gantry interval is shortened and an imaging gantry interval is provided, during which a minimal dose (e.g., 0.01 monitor units (MU)) required for a smooth gantry rotation is delivered. Currently, the linac control system for TrueBeam® can accept a RapicArc® plan with up to 500 CPs in a full 360 degree rotation. Therefore, the gantry interval for a dose and imaging CP pair is 1.44 degree. To work within the current mechanical/software constraints of the machine, the gantry intervals for the imaging CP and treatment CP and the gantry rotation speed are chosen to ensure sufficient minimal MV-scatter CBCT projections are acquired, while still delivering the dose plan as intended in minimal time. Table 1 sets out a list of example parameters that can be used in acquisition of kV-CBCT projections with minimum MV scattering, and Table 2 sets out comparisons of object-background contrast among different imaging scenarios.

TABLE 1

| Imaging mode | Plan MU | Imaging CP Gantry Interval (deg) | Number of projections with minimal scatter | Gantry Speed (deg/sec) | Delivery time (minutes) |
| --- | --- | --- | --- | --- | --- |
| Half-fan | 249 | 1.1 | 910 | 2.7 | 2.2 |
| Full-fan | 700 | 0.7 | 770 | 2.2 | 2.8 |

TABLE 2

| Imaging mode | KV-CBCT with full MV scatter ($CECT_c$) | KV-CBCT with minimum MV scatter ($CBCT_s$) | KV-CBCT without MV scatter ($CBCT_r$) |
| --- | --- | --- | --- |
| Full-fan | 6 | 12.1 | 12.3 |
| Half-fan | 2.8 | 7.0 | 7.1 |

The definition of a RapidArc® plan's control points initially exists in the treatment planning system. Once the additional imaging control points are added, the resultant file is converted to extensible markup language (XML), as required by the TrueBeam® for delivery. KV-CBCT imaging during treatment is then added to the XML file, as is a specification of the maximum gantry speed. The XML file is then ready for delivery in the TrueBeam® Developer Mode.

In one specific example, kV CBCT projections are continuously acquired during gantry rotation at a frequency of 11 frames/sec. In various test demonstrations of the system, the general imaging parameters were as follows: 125 kVp, 80 mA, 13 ms, for half-fan geometry, 100 kVp, 40 mA, 10 ms, for full-fan geometry, reconstructed at 2 mm slice thickness, and 512×512 pixel array. CBCT projections acquired during imaging control points were subject to minimal MV scatter and are sorted out based on gantry angle. These image projections reconstructed as "clean" CBCT images ($CBCT_s$) (with minimum MV scatter) using the Varian iTools™ software. Standard CBCT images ($CBCT_c$) acquired during and outside ($CBCT_r$) RapidArc® delivery serve as controls in evaluating the effectiveness of image quality improvement. Image quality was evaluated using the contrast-to-noise ratio, defined as the mean intensity of an object less background, divided by the standard deviation of the object intensity.

Figure 4:
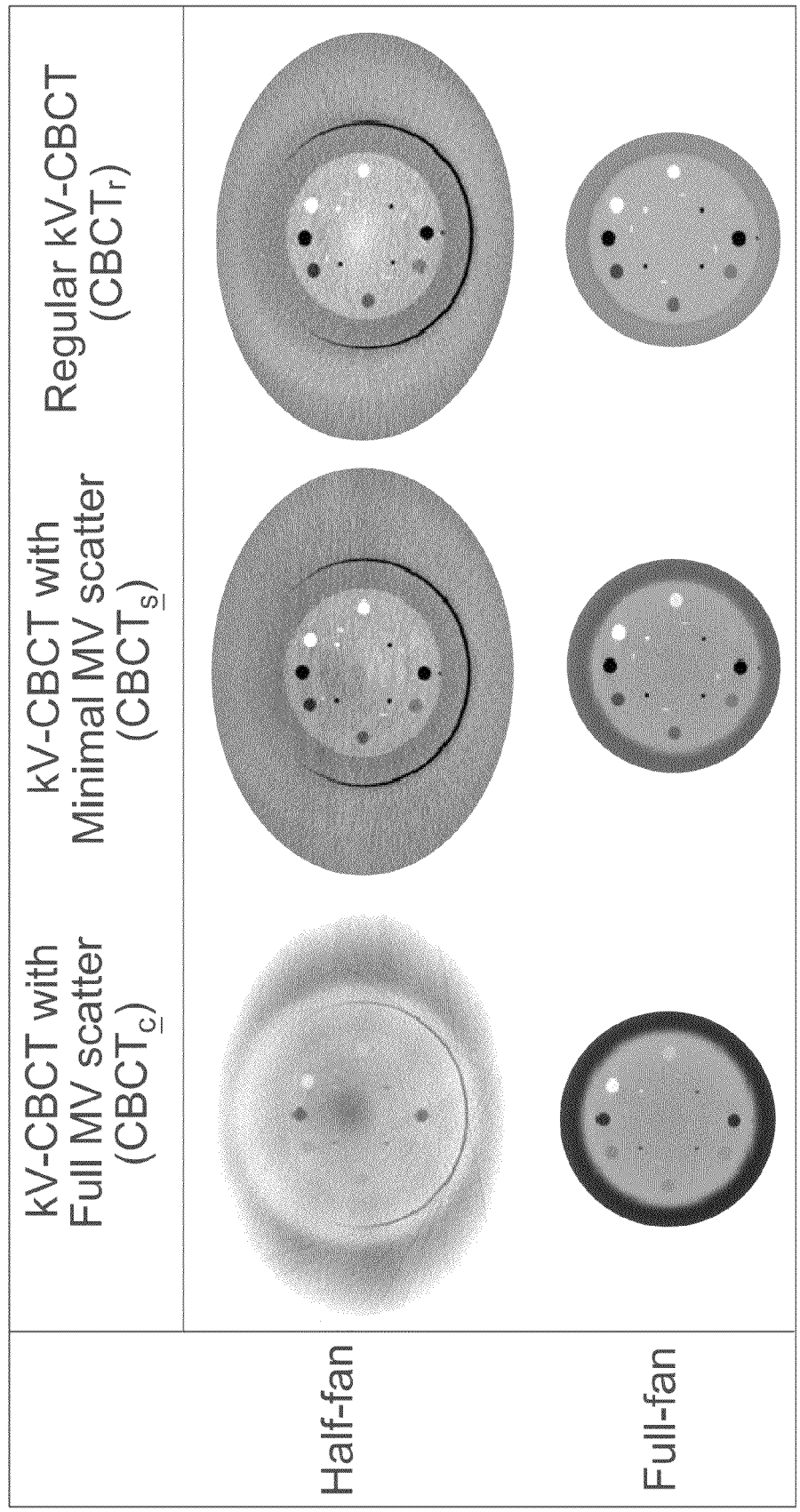
FIG. 4 depicts half-fan and full-fan imaging results of a test object using kilovoltage (kV) cone-beam computed tomography (CBCT) imaging, with full megavoltage (MV) scatter, minimum MV scatter, and with no MV scatter (i.e., regular kV-CBCT), in accordance with one or more aspects of the present invention.

Procedure time for $CBCT_s$ ranged from 2-3 minutes, comparable to a regular RapidArc® delivery plus a standard CBCT acquisition. In general, as illustrated in FIG. 4, the image quality of $CBCT_s$ is very comparable to $CBCT_r$. $CBCT_s$ images have less noise, and are more homogeneous compared to $CBCT_c$ images. Specifically, the low contrast circular object seen at the 5 o'clock position in the $CBCT_s$ and $CBCT_r$ images is not seen in the $CBCT_c$ image for either the half or full-fan mode. As seen in Table 2, object-background contrast ratios of $CBCT_s$ are comparable to $CBCT_r$, and 2-3 times higher than $CBCT_c$.

In another example, multiple instances of kV imaging may be added to the defined schedule (e.g., XML file), with one instance for each imaging control point. In this implementation, kV CBCT projections are acquired only during the low-dose imaging CP and therefore, no sorting of the projections is required. Typically, 2 to 3 kV CBCT projections may be acquired during each low-dose imaging CP. The precise timing of each kV CBCT projection acquisition is specified in the XML file. So, for example, a VMAT delivery may include a total of 470 CP with 235 CP for treatment and 235 CP for imaging. Assuming equal angular spacing for each imaging CP, instructions may be added to the XML file to acquire individual kV CBCT projections at fractional angular CP segments of, for example, 0.05, 0.3 and 0.7. In this example, 3 kV CBCT projections would be acquired during each imaging CP, for a total of 705 kV CBCT projections.

In the test demonstration, the general imaging parameters were as follows: 100 kVp, 50 mA, 10 ms, for full-fan geometry, 2 mm slice thickness, and 512×512 pixel array. Software manipulations were performed to combine the kV CBCT projections obtained from all imaging CP into a single acquisition, and the projections were then reconstructed using the Varian iTools™ software as a CBCT with minimal MV scatter.

As noted, a method is disclosed herein which truly integrates imaging and dose delivery. For example, kV CBCT images with minimal MV scatter can be acquired concomitantly with the treatment delivery with little overhead.

By way of further detail, and as introduced above, RapidArc®/CBCT treatment and imaging plans may be designed, and delivered on the Varian® TrueBeam®, using its Developer Mode. One plan might contain 250 control points for MV radiation delivery, each over an arc of 0.4-0.7°. Interlaced between successive MV delivery control points may be imaging control points, each (in one example) over an arc of 0.7-1.1°. During the 360° gantry rotation for the RapidArc® delivery, CBCT projections (e.g., of a phantom) may be acquired at 11 frames per second. The kV projections with minimal MV scatter are selected, based on gantry angle, and the $CBCT_s$ image reconstructed. For comparison, a reference $CBCT_r$ image is acquired in the normal way. In addition, to examine the effect of MV scatter, $CBCT_c$ may be acquired using the same treatment plan without the imaging control points, i.e. with continuous MV delivery during the 360° rotation. Quantitative evaluation of image qualities may be performed based on the concepts of CNR (contrast-to-noise ratio) and NSTD (normalized standard deviation).

The different types of CBCT images were reconstructed, evaluated, and compared. Visual comparison indicates that the image quality of $CBCT_s$ is similar to that of the reference $CBCT_r$, and that the quality of $CBCT_c$ is significantly degraded by the MV scatter. Quantitative evaluation of the image quality indicates that MV scatter significantly decreases the CNR of CBCT (from ~7 to ~3.5 in one comparison). Similarly, MV scatter significantly increases the inhomogeneity of image intensity, e.g. from ~0.03 to ~0.06 in one comparison.

There is increasing enthusiasm for the use of volumetric modulated arc therapy (VMAT) or RapidArc® in administrating intensity-modulated radiotherapy (IMRT). Studies have indicated that VMAT not only produces highly conformal dose distributions, similar to those of other forms of IMRT, but that it requires less MU and can be delivered in a shorter treatment time. Relative to the intra-fraction 'residual' uncertainties, the shorter treatment time of RapidArc® is beneficial. Advantageously, as disclosed herein, the use of a 360° gantry rotation in many RapidArc® treatment plans can accommodate the possibility of performing CBCT image acquisition during the actual radiation delivery session.

As noted, the treatment planning and delivery of RapidArc® may be based on the concept of control points (CP). To achieve conformal dose distribution, variable dose-rate, variable gantry speed, dynamic MLC movements are included in the optimization and delivery of radiation in each of the CPs. In the implementations of both Varian's RapidArc®, and VMAT at Memorial Sloan Kettering Cancer Center (MSKCC), 177 CPs are often used, equi-spaced over a 360° gantry rotation. To perform CBCT acquisition, concomitant with RapidArc® delivery, each CP may be divided, for example, into two or more CPs, with one or more CPs for MV radiation delivery and one or more CPs for acquiring kV projections or other imaging tasks. For example, several imaging CPs may be interjected into a single treatment CP, especially in the case of one or more long dose treatment CPs or segments (i.e., coarsely specified treatments, such as a treatment specified with one control point every 5 degrees). In such a case, and if desired, several imaging segments could be introduced between adjacent treatment control points or segments. During the imaging CP, the MV radiation beam is turned off to exclude MV-scatter in the kV projection images. However, this method requires synchronization between the processes for MV radiation delivery and kV image acquisition. Experiments were designed to demonstrate in proof of principle that CBCT images with negligible or near-zero MV-scatter can be acquired concomitantly with RapidArc® delivery.

In the Developer Mode, the Varian TrueBeam® uses the same control system as in the Clinical Modes, but enables access to additional advanced control features. Specifically, in the Developer Mode, the TrueBeam® system is driven by XML (extensible markup language) Beams loaded into the control console workstation computer. XML Beams are essentially text scripts in XML format in which a rich instruction set allows Developer Mode users to construct and implement complex non-standard beams and imaging processes. In this study, the ability of the Developer Mode to load and implement user-designed XML beams and imaging processes is used in performing the experiments to acquire MV-scatter-free CBCT images, as described below.

To demonstrate simultaneous RapidArc® delivery and CBCT acquisition plans were designed using 250 MV radiation delivery CPs, interlaced with 249 kV imaging CPs, such that each pair of MV+kV CPs corresponds to an average gantry angle of 1.44°, for a total gantry rotation of 357.8°. This choice is in part constrained by the Varian TrueBeam® which limits the total number of CP to be 500 or less. In the future, increasing the imaging CPs may be beneficial to improve the quality of the CBCT images.

By way of example, 6 MV photon beams may be used during the 250 radiation delivery CPs. In a first set of experiments, a fixed 10×10 cm field is used with 250 MU. The MV delivery is over a gantry angle of 0.4°, and the imaging CP over 1.0° or 1.1° (due to the 0.1° constraint in gantry angle setting). In a second set of experiments, to simulate clinical situations, a 325 MU VMAT plan for the treatment of a prostate tumor was used. In this case, the MV delivery was over a gantry angle of 0.7°, and the imaging CP over 0.7° or 0.8°. The MV delivery CP was over a wider gantry angle because of the longer time needed for intensity modulated beams.

During each of the imaging CP, delivery of 0.01 MU was specified. This, in addition to the specification of gantry speed (see below), was necessary to avoid uneven gantry rotation speed during the treatment and imaging control points, respectively. Although MV-scatter (from the 0.01 MU per imaging CP) will attend the CBCT projection images, its magnitude is ≤1% of that from 250 and 325 MU over ~360° gantry rotation. Nevertheless, the term of "MV-scatter free CBCT" in this document should be regarded with this qualification.

As proof of principle, kV CBCT projections were continuously acquired during gantry rotation at, by way of example, a frequency of 11 frames/sec. The imaging parameters were as follows: half-fan geometry, 125 kVp, 80 mA, 13 ms exposures, with 2 mm slice thickness, and reconstructed into a 512×512×80 voxel array. The Phantomlab Catphan 504 phantom (marketed by The Phantom Laboratory of Salem, N.Y., USA) with elliptical expansion was placed at the isocenter. This phantom has inserts of materials with different densities (polystyrene, acrylic, Delrin, Teflon, Air, and polymethylpentene, polyethylene etc.), and is ideal for evaluation of CBCT image quality. The elliptical expansion measures 38×30×20 cm in the lateral, AP-PA and vertical dimensions, and is a reasonable simulation of the pelvis of a patient.

To ensure that sufficient number of MV-scatter free CBCT projections were acquired within the imaging CP, the maximum gantry speed was set at 2.7°/sec for the 250 MU (10×10 cm) delivery, and 2.2°/sec for the 325 MU RapidArc® delivery, wherein 10×10 cm is the treatment field size at isocenter, or 1 meter from the MV source. This experimental design ensures near-uniform gantry speed over the 360° rotation for both plans. In the implementation on the TrueBeam®, ~2.1 min was needed for the 250 MU (10×10 cm) plan, and ~2.7 min for the 325 MU RapidArc® plan, respectively.

Figure 5:
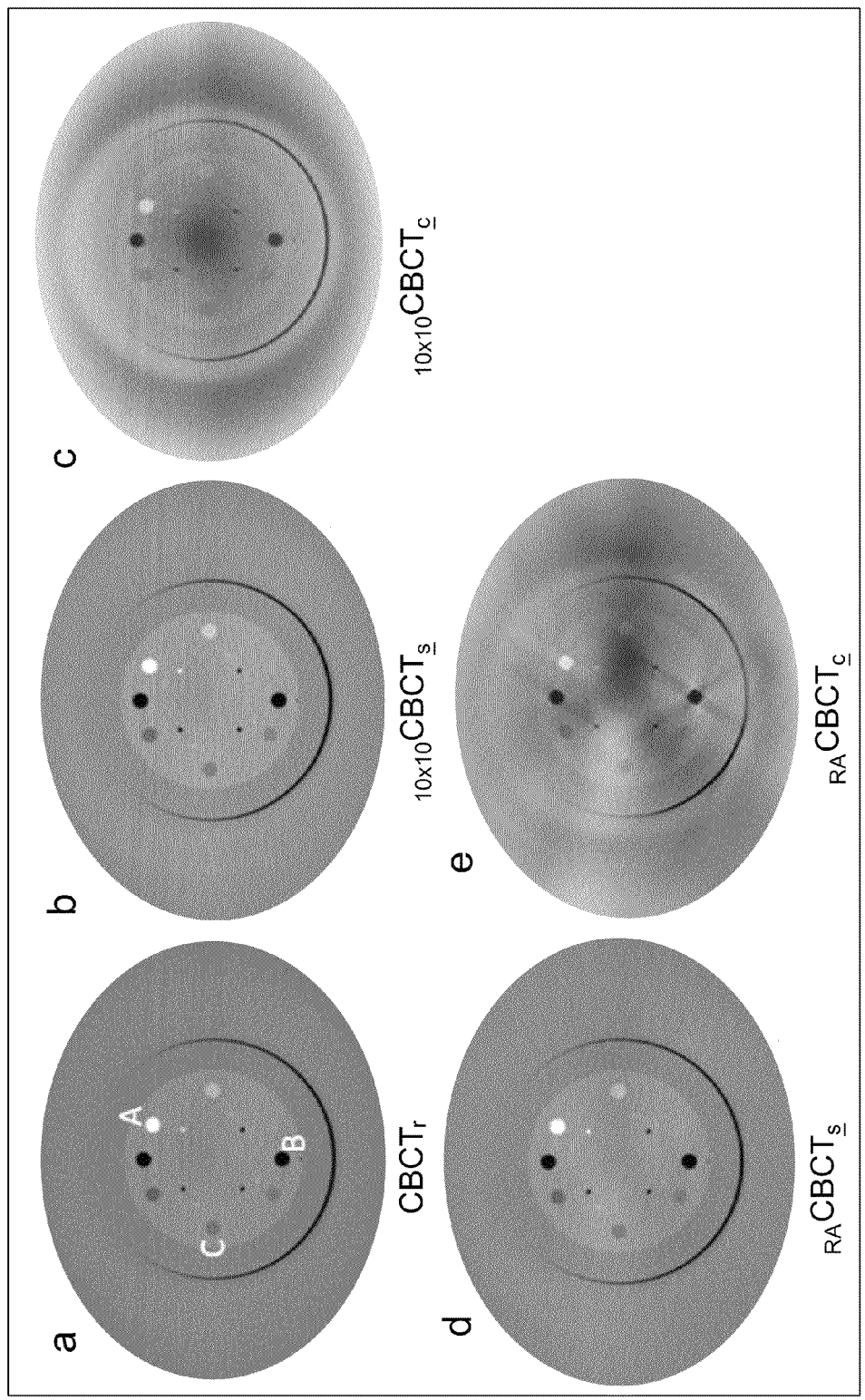
FIG. 5 depicts further imaging results of the test object experimentally obtained in verifying practical operation of an arc radiotherapy and imaging system, in accordance with one or more aspects of the present invention.

Standard CBCT Image of Catphan 504:

As a basis for comparison a standard or reference CBCT image ((a) in FIG. 5) was obtained, i.e. with kV imaging only, using the manufacturer's pelvis imaging protocol, i.e. half-fan geometry, 125 kVp, 80 mA, 13 ms, 660 projections for a total of 680 mAs, reconstructed at 2 mm slice thickness into a 512×512×80 voxel array. The standard CBCT image was acquired in ~60 seconds.

Extraction of MV Scatter-Free Projections:

For the 250 MU 10×10 cm plan, a total of ~1470 kV projections were obtained, with ~1020 within the imaging CP, or ~4 projections per imaging CP. For comparison with the standard CBCT with 660 projections, on average 2.64 projections are selected per imaging CP. The selection of CBCT projections was based on the gantry angle recorded on each projection. The first projection was discarded immediately after the MV CP, which may contain MV scatter. From the $2^{nd}$ to $4^{th}$ projections, 2 or 3 projections were selected for an average of 2.64 projections per imaging CP, with approximately equi-spacing over the 360° gantry rotation. A similar procedure was followed for the 325 MU prostate RapidArc® plan, except that 770 kV projections were selected (for comparison with data acquired with MV scatter, as described below).

The Effect of MV Scatter on CBCT Images:

To examine the effect of MV scatter from RapidArc® delivery on CBCT images, additional experiments were performed. Specifically, the same treatment was delivered with no imaging CPs. The delivery of the 250 MU 10×10 cm treatment was performed in ~60 sec and provided ~660 kV projections. The 325 MU RapidArc® prostate plan was delivered in ~70 sec, generating ~770 kV projections. In both cases, the kV projections were acquired with the MV radiation beam being 'on'.

Reconstruction and Evaluation of CBCT Images:

CBCT images were reconstructed using the adaptive deconvolution algorithm in the Varian iTool® software v1.0. Image quality was evaluated in terms of: (a) the CNR (contrast-to-noise ratio), and (b) the NSTD (normalized standard deviation), a surrogate of image inhomogeneity, defined as the standard deviation divided by the mean intensity of the entire image.

To summarize, 5 types of CBCT images were acquired, reconstructed, and evaluated in this experiment, as illustrated in FIG. 5: a) standard CBCT as a reference ($CBCT_r$), b) MV scatter-free CBCT acquired during the imaging CP with 10×10 cm MV beam ($_{10\times10}CBCT_s$), c) CBCT with MV scatter from the 10×10 cm MV beam ($_{10\times10}CBCT_c$), d) MV scatter-free CBCT acquired during the imaging CP with RapidArc® prostate treatment ($_{RA}CBCT_s$), e) CBCT with MV scatter from the RapidArc® prostate treatment ($_{RA}CBCT_c$), In FIG. 5, $CBCT_r$—the reference CBCT, was reconstructed from 660 projections; $_{10\times10}CBCT_s$—MV scatter-free CBCT for the 10×10 cm MV beam, was reconstructed from 660 projections; $_{10\times10}CBCT_c$—CBCT with MV scatter for the 10×10 cm MV beam, was reconstructed from 660 projections $_{RA}CBCT_s$—MV scatter-free CBCT for the prostate RapidArc® treatment, was reconstructed from ~770 projections; and $_{RA}CBCT_c$—CBCT with MV scatter for the prostate treatment RapidArc®, was reconstructed from ~770 projections.

Visual inspection of FIG. 5 indicates that MV scatter significantly degrades the kV CBCT images. Specifically, the image quality of $_{10\times10}CBCT_c$ is much worse than that of $_{10\times10}CBCT_s$, and the image quality of $_{RA}CBCT_c$ is much inferior to that of $_{RA}CBCT_s$. For example, the low contrast object at the 7 o'clock position is clearly visible in the $_{10\times10}CBCT_s$ and $_{RA}CBCT_s$ images, barely visible in $_{10\times10}CBCT_c$, and not at all in $_{RA}CBCT_c$.

Visual comparison also indicates that the image quality of $_{10\times10}CBCT_s$ is similar to that of the reference $CBCT_r$, and that of $_{RA}CBCT_s$ perhaps slightly inferior, providing strong evidence that CBCT with minimal MV-scatter can be acquired during treatment delivery.

There are halo artifact (dark circles surrounding the central phantom) and horizontal streaking artifacts, which are prominent in the $_{10\times10}CBCT_c$ image. Upon closer examination, the horizontal streaking artifacts are also visible in the $_{10\times10}CBCT_s$, but much less prominent. There is a similar but reduced halo artifact in the $_{RA}CBCT_c$ image, and prominent 'spoke' artifacts at ~2, 7 and 11 o'clock positions. These artifacts presumably are from the MV scatter.

Results of quantitative evaluation of the CBCT image qualities, based on the concepts of CNR (contrast-to-noise ratio) and NSTD (normalized standard deviation), are presented in Table 3 below. For the CNR analysis, the same three objects in each image (A, B, C in FIG. 5) are evaluated and the results listed in Table 3. MV scatter significantly decreases the CNR of the CBCT image. For example, the CNR of object A is ~6-7 in $CBCT_r$, $_{10\times10}CBCT_s$ and $_{10\times10}CBCT_s$, and ~3.5 in $_{10\times10}CBCT_c$ and $_{RA}CBCT_c$ images. The same conclusion, that MV scatter decreases CNR, applies to the analysis of objects B and C.

As expected, MV scatter significantly increases the inhomogeneity of the CBCT image intensity. Specifically, the NSTD is about 0.03 for $CBCT_r$, $_{10\times10}CBCT_s$, and $_{RA}CBCT_s$, and 0.06 for the $_{10\times10}CBCT_c$ and $_{RA}CBCT_c$ images.

As discussed herein, the $CBCT_r$, $_{10\times10}CBCT_s$ and $_{10\times10}CBCT_c$ images were reconstructed from 660 kV-projections, and the $_{RA}CBCT_s$, and $_{RA}CBCT_c$ images from ~770 kV-projections. Based on visual comparison of the panels of FIG. 5, this difference in number of projections did not result in observable changes in image quality between $CBCT_r$, $_{10\times10}CBCT_s$ and $_{RA}CBCT_s$.

To summarize, disclosed herein (in one embodiment) is a method of obtaining CBCT images, which have either zero or minimal MV scatter, concomitant with RapidArc® or VMAT delivery. The method may be based on the concept of interlacing MV delivery and kV imaging control points during the 360° gantry rotation such that the kV CBCT projections are devoid of MV scatter. Experimental results demonstrate the capability of this approach to acquire MV scatter-free CBCT images during RapidArc® treatment. As discussed above, both visual assessment and quantitative evaluation indicates that the $CBCT_s$ images are of similar quality as the $CBCT_r$ image. In contrast, the image quality of $CBCT_c$ is significantly degraded by MV scatter.

The above-discussed proof-of-principle illustrating that MV scatter-free CBCT images can be obtained concomitant with RapidArc® delivery, was implemented on the Varian TrueBeam® using its Developer mode. For eventual clinical implementation, the following are examples of specific objectives to be considered: 1) the requirement for kV CBCT should be planned in terms of image quality; 2) the imaging dose should be minimized by restricting kV projections to within the imaging CP; 3) the efficiency of the overall process should be optimized by synchronizing the MV and imaging CP; and 4) the efficiency of MV delivery should be increased by treatment plan optimization and by the use of high-intensity (flattening-filter-free) radiation beams.

While clinical criteria and protocols for image guidance during radiotherapy delivery are still evolving, CBCT obtained during a radiotherapy session will gain momentum as a useful tool. As noted above, pre-treatment CBCT can be used to increase set-up accuracy. In addition, the "session" CBCT may be compared to the planning CT images or overlaid with delivered dose distribution to facilitate adaptive radiotherapy. Up to now, such "session" CBCT images were acquired either before or after radiation delivery, and therefore cannot take into account the intra-fraction changes in target position during a radiotherapy session. Adaptive therapy based on such images is therefore subject to 'residual' uncertainties resulting from intra-fraction organ movement. In this regard, CBCT images obtained concomitantly with radiation delivery may offer some improvement, in that they yield actual anatomical data on which the delivered dose distribution can be superimposed and examined.

Whether a CBCT is acquired prior to treatment, or concomitantly with RapidArc® delivery, the image quality will be negatively affected by organ motion. Thus, the CBCT acquired using the approach disclosed herein is also affected by intra-fraction organ motion. On this point, the relatively

TABLE 3

|  |  | $CBCT_r$ | $_{10\times10}CBCT_s$ | $_{10\times10}CBCT_c$ | $_{RA}CBCT_s$ | $_{RA}CBCT_c$ |
|---|---|---|---|---|---|---|
| CNR | Object A | 6.7 | 6.8 | 3.7 | 6.8 | 3.4 |
|  | Object B | 36.4 | 30.9 | 7.2 | 30.9 | 14.1 |
|  | Object C | 5.3 | 4.9 | 1.2 | 5.1 | 1.9 |
|  | NSTD | 0.03 | 0.03 | 0.06 | 0.03 | 0.06 | short treatment time of RapidArc® is beneficial. In the present design, a 1.8 Gy and 360° rotational treatment can be delivered, concomitant with CBCT acquisition, in ~2-3 min. With the previously-noted improvements, the combined treatment/imaging time could be reduced to ~1.5 min, as compared to ~1 min for a standard CBCT for the pelvis. Given that the increase in time is only ~0.5 min, the increase in the detrimental effect of intra-fraction organ motion should not be severe.

If the quality of a CBCT image acquired during RapidArc® is degraded due to organ motion, as judged by comparison with a reference image, it may be possible to extract information of the motion using digital tomosynthesis (DTS). In this approach, a series of DTS images can be constructed using the projection images in respective gantry angle segments, and examined to detect positional shifts of discernable structures.

An important current trend in radiotherapy is towards smaller number of fractions in a treatment course, using either hypofractionation, or oligo-fractionation in stereotaxic body radiotherapy (SBRT) approach. The RapidArc®/CBCT approach may be of particular interest and importance for oligo-fractionation radiotherapy in which a large dose is delivered per treatment session, e.g., 10-24 Gy in a treatment session. For such treatments, treatment delivery may be divided into sub-treatments (e.g., 4 sub-treatments of 6 Gy for a single 24 Gy SBRT), each delivered using the RapidArc®/CBCT. After each sub-treatment the acquired CBCT can be examined to assure anatomical accuracy prior to the next sub-treatment.

Figure 6:
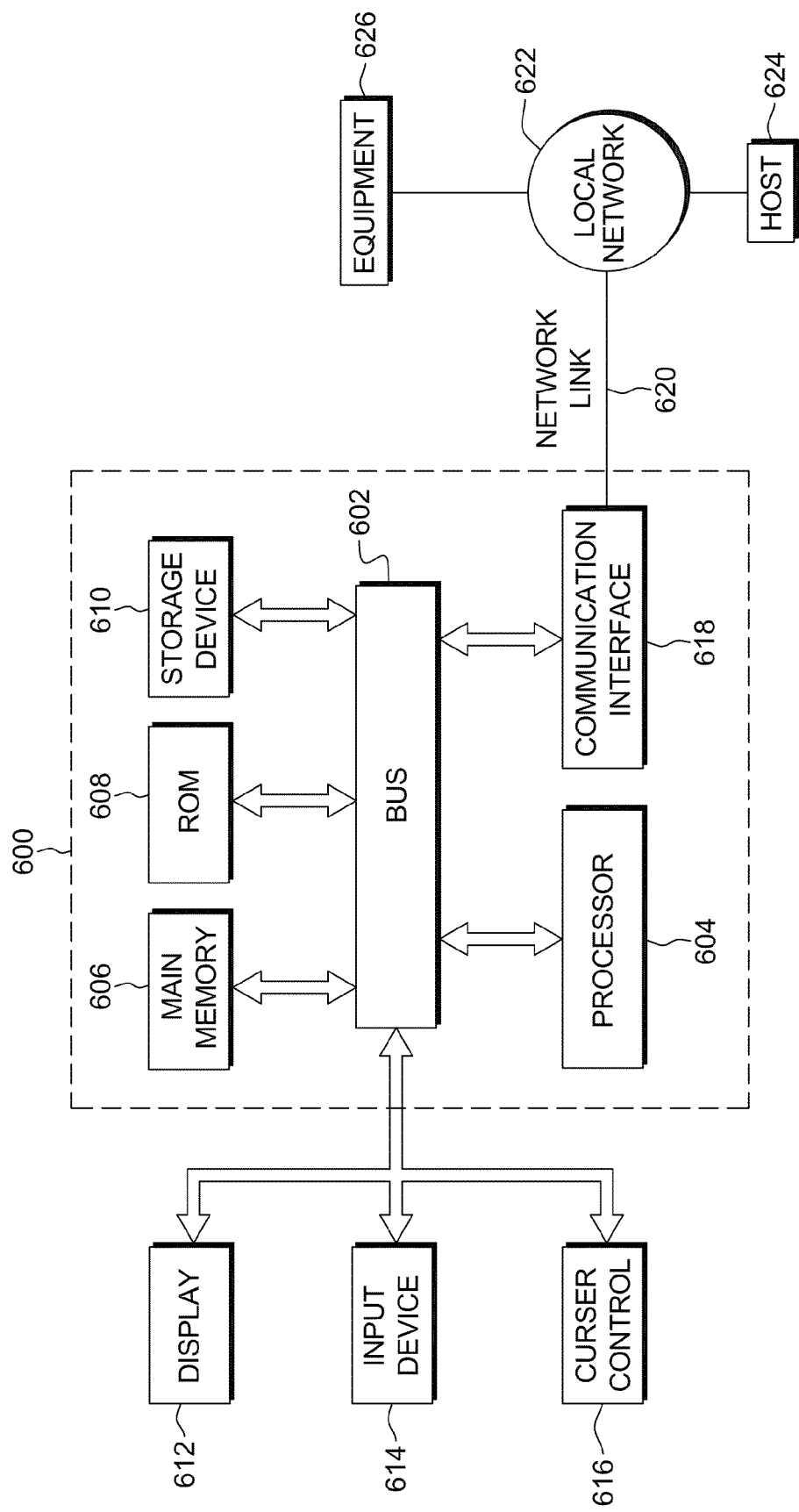
FIG. 6 illustrates a block diagram of a computer system that can be employed in controlling an arc radiotherapy and imaging system, in accordance with one or more aspects of the present invention.

FIG. 6 is a block diagram illustrating an embodiment of a computer system 600 that can be used to implement various embodiments of the processing described herein. Computer system 600 includes a bus 602 or other communication mechanism for communicating information, and a processor 604 coupled with the bus 602 for processing information. Computer system 600 also includes a main memory 606, such as a random access memory (RAM) or other dynamic storage device, coupled to bus 602 for storing information and instructions to be executed by processor 604, and a read only memory (ROM) 608 or other static storage device coupled to bus 602 for storing static information and instructions for processor 604. A data storage device 610, such as a magnetic disk or optical disk, is provided and coupled to bus 602 for storing information and instructions.

Computer system 600 may be coupled via bus 602 to a display 617, for displaying information to a user. An input device 614, for example, including alphanumeric and other keys, is coupled to bus 602 for communicating information and command selections to processor 604. Another type of user input device is a cursor control 616, such as a mouse, a trackball, or cursor direction keys, for communicating direction information and command selections to processor 604 and for controlling cursor movement on display 617. This input device typically has two degrees of freedom in two axes, a first axis (e.g., x) and a second axis (e.g., y), that allows the device to specify positions in a plane.

In some embodiments, the computer system 600 can be used to perform various functions described herein. According to certain embodiments of the invention, such use is provided by computer system 600 in response to processor 604 executing one or more sequences of one or more instructions contained in main memory 606. Those skilled in the art will know how to prepare such instructions based on the functions and methods described herein. Such instructions may be read into main memory 606 from another computer-readable medium, such as storage device 610. Execution of the sequences of instructions contained in the main memory 606 causes the processor 604 to perform the process steps described herein. One or more processors in a multi-processing arrangement may also be employed to execute the sequences of instructions contained in the main memory 606. In alternative embodiments, hard-wired circuitry may be used in place of or in combination with software instructions to implement the invention. Thus, embodiments of the invention are not limited to any specific combination of hardware circuitry and software.

Computer system 600 also includes a communication interface 618 coupled to the bus 602, which provides a two-way data communication coupling to a network link 620 that is connected to a local network 622. For example, the communications interface 618 may be an integrated services digital network (ISDN) card or a modem to provide a data communication connection to a corresponding type of telephone line. As another example, the communication interface 618 may be a local area network (LAN) card to provide a data communication connection to a compatible LAN. Wireless links may also be implemented. In any such implementation, the communication interface 618 sends and receives electrical, electromagnetic or optical signals that carry data streams representing various types of information.

The network link 620 typically provides data communication through one or more networks to other devices. For example, the network link 620 may provide connection through local network 622 to a host computer 624 or to equipment 626, such as any of the devices described herein, or a switch operatively coupled to any of the devices described herein. The data streams transported over the network link 620 can comprise electrical, electromagnetic of optical signals. The signals through the various networks and the signals on the network link 620 and through communication interface 618, are exemplary forms of carrier waves transporting the information. The computer system 600 can send messages and receive data, including program code, through the network(s), the network link 620, and the communication interface 618.

As will be appreciated by one skilled in the art, various aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system". Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable signal medium may include a propagated data signal with computer readable program code embodied therein, for example, in baseband or as part of a carrier wave. Such a propagated signal may take any of a variety of forms, including, but not limited to, electromagnetic, optical or any suitable combination thereof. A computer readable signal medium may be any computer readable medium that is not a computer readable storage medium and that can communicate, propagate, or transport a program for use by or in connection with an instruction execution system, apparatus or device.

A computer readable storage medium may be, for example, but not limited to, an electronic, magnetic, optical, electromagnetic, infrared or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain or store a program for use by or in connection with an instruction execution system, apparatus, or device.

Figure 7:
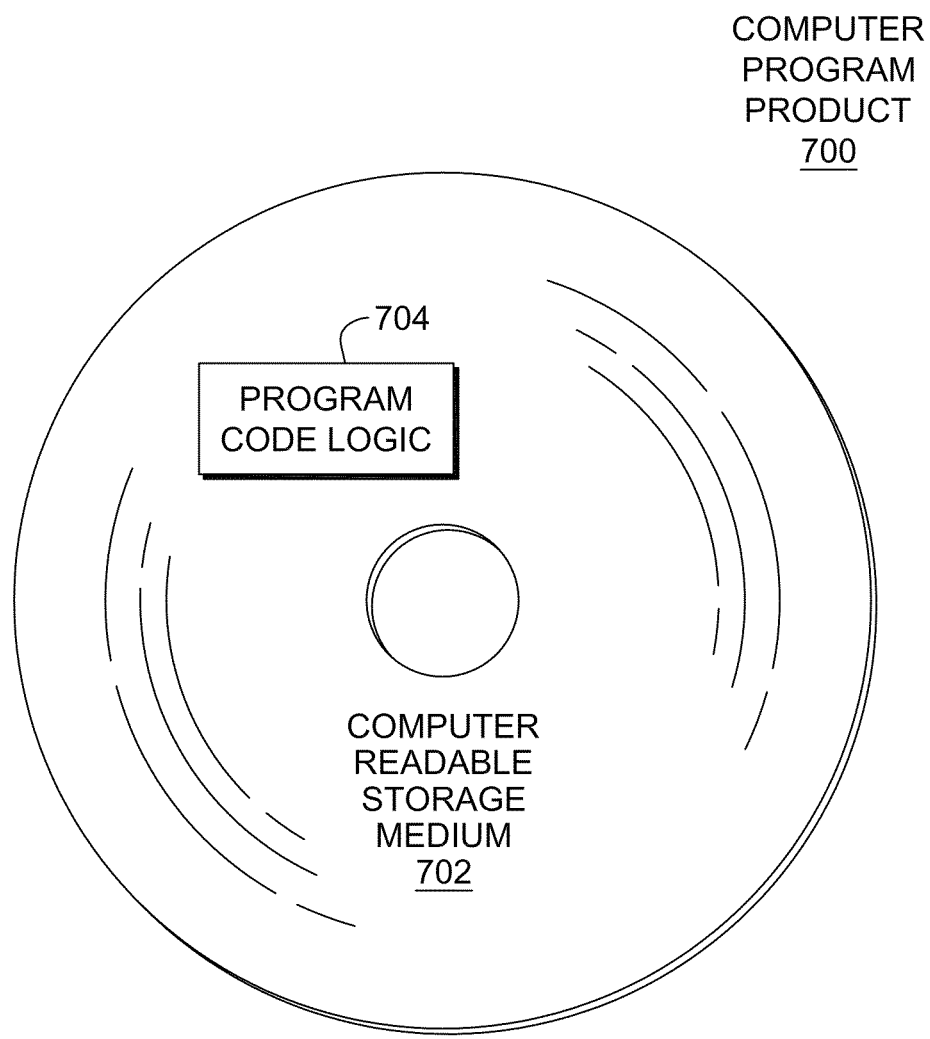
FIG. 7 depicts one embodiment of a computer program product incorporating one or more aspects of the present invention.

Referring to FIG. 7, in one example, a computer program product 700 includes, for instance, one or more computer readable storage media 702 to store computer readable program code means or logic 704 thereon to provide and facilitate one or more aspects of the present invention.

Program code embodied on a computer readable medium may be transmitted using an appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language, such as Java, Smalltalk, C++ or the like, and conventional procedural programming languages, such as the "C" programming language, assembler or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features. Furthermore, a device or structure that is configured in a certain way is configured in at least that way, but may also be configured in ways that are not listed.

Although particular embodiments of the present inventions have been shown and described, it will be understood that it is not intended to limit the present inventions, and it will be obvious to those skilled in the art that various changes and modifications may be made without departing from the spirit and scope of the present inventions. For example, the term "image" or "image data", as used in this specification, includes image data that may be stored in a circuitry or a computer-readable medium, and should not be limited to image data that is displayed visually. Also, it should be noted that in other embodiments, the radiation system may not include one or more of the components described herein. In addition, in other embodiments, the radiation system may include any of the components described herein, even if the components are described as separate elements from the radiation system.

What is claimed is:

1. An arc radiotherapy and imaging system comprising:
a first radiation system suitable for treating a region of a patient;
a second radiation system suitable for imaging the region of the patient;
an accelerator gantry having a rotary portion which moves in arc segments, wherein the first radiation system and the second radiation system are associated, at least in part, with the rotary portion of the accelerator gantry; and
a control for automatically adjusting system operation according to a defined schedule between treating the region of the patient using the first radiation system and imaging the region of the patient using the second radiation system, wherein the control automatically adjusts operation between arc segments of the accelerator gantry responsive to a predefined series of interspersed treatment control points and imaging control points, the treatment control points and imaging control points of the predefined series being associated with different arc segments of the accelerator gantry, and wherein the control automatically switches operation responsive to a treatment control point of the predefined series to treating the region of the patient using the first radiation system, and automatically switches operation responsive to an imaging control point of the predefined series to imaging the region of the patient using the second radiation system.

2. The arc radiotherapy and imaging system of claim 1, wherein at least a portion of the predefined series alternates between treatment control points and imaging control points.

3. The arc radiotherapy and imaging system of claim 1, wherein at least a portion of the predefined series includes regularly spaced imaging control points.

4. The arc radiotherapy and imaging system of claim 1, wherein at least a portion of the predefined series includes irregularly spaced imaging control points.

5. The arc radiotherapy and imaging system of claim 1, wherein the treatment control points and the imaging control points are interwoven in a repeating pattern within at least a portion of the predefined series.

6. The arc radiotherapy and imaging system of claim 1, wherein the first radiation system delivers any one of a volume modulated arc therapy treatment or an intensity modulated radiation therapy treatment, and the second radiation system comprises part of an imaging system for imaging the region of the patient, the imaging system acquiring any one of kilovoltage cone-beam computed tomography projections or megavoltage cone-beam computed tomography projections of the region of the patient.

7. The arc radiotherapy and imaging system of claim 1, wherein during treating the region of the patient using the first radiation system, one or more treatment doses of radiation are provided by the first radiation system for treating the region of the patient, and during imaging the region of the patient, no treatment dose of radiation is provided by the first radiation system to the region of the patient being imaged using the second radiation system.

8. The arc radiotherapy and imaging system of claim 1, wherein the first radiation system delivers a megavoltage x-ray beam as the accelerator gantry moves around the region of the patient, and the second radiation system delivers any one of a kilovoltage cone-beam or a megavoltage cone-beam as the accelerator gantry moves around the region of the patient, the second radiation system comprising part of an imaging system, and the imaging system facilitating obtaining computed tomography images interwoven with delivery of treatment doses via the first radiation system to the region of the patient.

9. The arc radiotherapy and imaging system of claim 1, wherein the control automatically compresses one or more arc segments of the accelerator gantry for treating the region of the patient using the first radiation system to provide one or more arc segments of the accelerator gantry for imaging the region of the patient using the second radiation system.

10. A method of fabricating an arc radiotherapy and imaging system comprising:
providing a first radiation system suitable for treating a region of a patient;
providing a second radiation system suitable for imaging the region of the patient;
providing an accelerator gantry having a rotary portion which moves in arc segments, wherein the first radiation system, and the second radiation system are associated, at least in part, with the rotary portion of the accelerator gantry; and
providing a control for automatically adjusting system operation according to a defined schedule between treating the region of the patient using the first radiation system and imaging the region of the patient using the second radiation system, wherein the control automatically adjust operation between arc segments of the accelerator gantry responsive to a predefined series of interspersed treatment control points and imaging control points, the treatment control points and imaging control points of the predefined series being associated with different arc segments of the accelerator gantry, and wherein the control automatically switches operation responsive to a treatment control point of the predefined series to treating the region of the patient using the first radiation system, and automatically switches operation responsive to an imaging control point of the predefined series to imaging the region of the patient using the second radiation system.

11. The method of claim 10, wherein at least a portion of the predetermined series alternates between treatment control points and imaging control points.

12. The method of claim 10, wherein at least a portion of the predefined series includes regularly spaced imaging control points.

13. The method of claim 10, wherein at least a portion of the predefined series includes irregularly spaced imaging control points.

14. The method of claim 10, wherein the treatment control points and the imaging control points are interwoven in repeating pattern within at least a portion of the predefined series.

15. The method of claim 10, wherein the first radiation system delivers any one of a volume modulated arc therapy treatment or an intensity modulated radiation therapy treatment, and the second radiation system comprises part of an imaging system for imaging the region of the patient, the imaging system acquiring any one of kilovoltage cone-beam computed tomography projections or megavoltage cone-beam computed tomography projections of the region of the patient.

16. The method of claim 10, wherein during treating the region of the patient using the first radiation system, one or more treatment doses of radiation are provided by the first radiation system for treating the region of the patient, and during imaging the region of the patient, no treatment dose of radiation is provided by the first radiation system to the region of the patient being imaged using the second radiation system.

17. The method of claim 10, wherein the first radiation system delivers a megavoltage x-ray beam as the accelerator gantry moves around the region of the patient, and the second radiation system delivers any one of a kilovoltage cone-beam or a megavoltage cone-beam as the accelerator gantry moves around the region of the patient, the second radiation system comprising part of an imaging system, and the imaging system facilitating obtaining computed tomography images interwoven with delivery of treatment doses via the first radiation system to the region of the patient.

18. The method of claim 10, wherein the control automatically compresses one or more arc segments of the accelerator gantry for treating the region of the patient using the first radiation system to provide one or more arc segments of the accelerator gantry for imaging the region of the patient using the second radiation system.

* * * * *